(12) United States Patent
Patterson

(10) Patent No.: US 6,186,965 B1
(45) Date of Patent: Feb. 13, 2001

(54) DISSOLVABLE SEPTAL SPLINT AND METHOD OF USING THE SAME

(75) Inventor: Matthew C. Patterson, Minneapolis, MN (US)

(73) Assignee: Acoustic Technologies, Inc., Minneapolis, MN (US)

( * ) Notice: Under 35 U.S.C. 154(b), the term of this patent shall be extended for 0 days.

(21) Appl. No.: 09/261,379

(22) Filed: Mar. 3, 1999

(51) Int. Cl.⁷ .................................................... A61B 17/00
(52) U.S. Cl. ................... 602/5; 602/6; 606/199
(58) Field of Search ..................... 606/199; 602/5, 602/6

(56) References Cited

U.S. PATENT DOCUMENTS

| | | |
|---|---|---|
| 4,378,802 | 4/1983 | Ersek . |
| 4,592,357 | 6/1986 | Ersek . |
| 4,650,488 | 3/1987 | Bays et al. . |
| 5,350,580 | 9/1994 | Muchow et al. . |
| 5,584,799 | 12/1996 | Gray . |

FOREIGN PATENT DOCUMENTS

3933217 * 4/1991 (DE) .

* cited by examiner

Primary Examiner—Michael H. Thaler
(74) Attorney, Agent, or Firm—Merchant & Gould P.C.

(57) ABSTRACT

A septal splint that does not require surgical removal after implantation. The septal splint is designed to be dissolvable over a period of time, thereby eliminating the need to surgically remove the splint. Preferably, the splint dissolves within four weeks after placement. The dissolvable splint of the invention allows surgeons that provide services to rural and small medical facilities at infrequent intervals, such as once per month, to perform septoplasty procedures without requiring the surgeons to make special arrangements for follow-up visits to remove the splints. Furthermore, the dissolvable splint eliminates the need for a splint removal procedure, which is particularly difficult to perform with children.

18 Claims, 2 Drawing Sheets

DISSOLVABLE SEPTAL SPLINT AND METHOD OF USING THE SAME

FIELD OF THE INVENTION

The invention relates to the field of implantable splints, and more particularly relates to a dissolvable splint for supporting a septum, such as a nasal septum, as well as to a method for supporting a septum utilizing a pair of the dissolvable splints. The dissolvable splint has particular use for supporting the septum of the nose after it has been surgically repaired with a septoplasty procedure.

BACKGROUND OF THE INVENTION

The purpose of any septal splint is to provide stability and support to a septum, particularly while the septum is healing after a surgical procedure thereon. One common use of a septal splint is to support a nasal septum while it is healing after performing a septoplasty procedure. Typically, one septal splint is placed on each side of the nasal septum, and then the splints are secured into position using a non-dissolvable suture that traverses the nasal septum and each of the splints. The splints prevent the nasal septum from healing in a bent or curved position. The splints are thereafter removed within 5–10 days, along with the non-dissolvable suture.

A second purpose of the splints is to prevent blood from accumulating within the nasal septum after surgery has been performed. The two splints are pulled tightly together by the suture, squeezing the nasal septum therebetween. This prevents a septal hematoma from accumulating between the two reapproximated mucosal surfaces of the nasal septum. If such a hematoma does form, an infection may occur, which could result in the injury of the cartilaginous support structure of the nose, and thereby possibly result in the collapse of the nose.

However, conventional septal splints have to be removed after a period of time, typically 5–10 days, thereby necessitating that the patient return to the doctor for a follow-up visit for splint removal. In rural areas and small medical facilities at which a surgeon may visit at infrequent intervals, such as once per month, the requirement for a follow-up visit after implanting the septal splints can be problematic, and often times requires that special arrangements be made to permit the splint removal. Similarly, in cases where a patient must travel long distances to have surgery performed, the patient is required to make an additional trip back to their surgeon for splint removal. Furthermore, removal of septal splints can be difficult, particularly from children for whom such a procedure can be especially traumatic.

What is needed then is an improved septal splint and method of using the same that solves many of the problems of conventional septal splints, as well as providing additional benefits not found in existing septal splints.

SUMMARY OF THE INVENTION

The invention provides an improved septal splint that does not require removal after implantation. The septal splint is designed to be dissolvable over a period of time, thereby eliminating the need to remove the splint. Preferably, the splint dissolves within four weeks after placement. The dissolvable splint of the invention allows surgeons that provide services to rural and small medical facilities at infrequent intervals, such as once per month, to perform septoplasty procedures without requiring the surgeons to make special arrangements for follow-up visits to remove the splints. Furthermore, the dissolvable splint eliminates the need for a splint removal procedure.

In one embodiment in accordance with the invention, a septal splint for supporting a septum is provided which comprises a body having first and second side faces and a peripheral edge extending between the first and second side faces. One of the first and second side faces is substantially planar to enable disposition against the septum. The body is formed of a bioerodable material whereby the body does not have to be surgically removed.

In another embodiment in accordance with the invention, a method of supporting a septum is provided which comprises providing a pair of septal splints each of which is made of a bioerodable material; positioning the septal splints on each side of the septum; securing the septal splints in place with the septum disposed therebetween; and allowing the septal splints to dissolve over a period of time.

In yet another embodiment in accordance with the invention, a dissolvable splint to be surgically implanted for supporting body tissue is provided. The splint comprises a body having first and second side faces and a peripheral edge extending between the first and second side faces. The body is shaped to abut the body tissue and provide support thereto. The body is formed of a bioerodable material whereby the splint does not have to be surgically removed once it is surgically implanted.

The preferred bioerodable material that is used to form the septal splint is collagen, which is a natural architectural component of the tissues of the human body. The collagen can be in the form of a gelatin material that is prepared and manufactured in various ways, thus allowing for the creation of a generally rigid, slightly malleable splint that has some measure of elasticity and memory of structure. The characteristics allow for the splint to be temporarily deformed upon the application of significant force during the positioning of the splint. However, upon removal of the force, the splint will return to its original configuration, thus providing a rigid support for the tissue to which it is attached. One suitable gelatin material is called GELFILM®.

Another advantage of the dissolvable septal splint is that it can be impregnated with various materials that enhance the capabilities of the splint. In one version, the splint can be impregnated with gluteraldehydes to vary the rate at which the splint dissolves. The splint can also be impregnated with antibiotics which will be released in the area of the septum as the splint dissolves, thereby assisting in the prevention of post-operative infection.

A variety of additional advantages of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

Referring now to the drawings wherein like reference numerals indicate corresponding parts throughout the several views.

DETAILED DESCRIPTION OF THE PREFERRED EMBODIMENT

Figure 1:
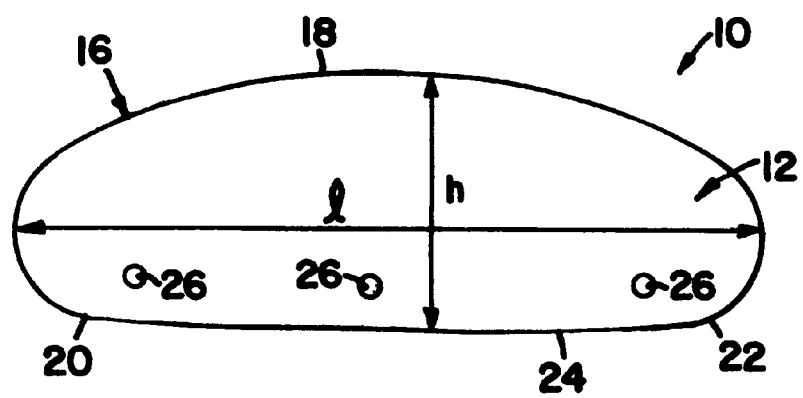
FIG. 1 is a side view of the septal splint in accordance with the principles of the invention.

The invention relates to a dissolvable splint that is to be surgically implanted into a human or animal body for supporting body tissue. The splint is shaped to abut against the tissue that it is intended to support, and is made from a bioerodable material to enable the splint to dissolve over a period of time after placement against the tissue, thereby eliminating the need for a splint removal procedure.

The splint is specifically described and shown herein as being for use with a nasal septum, however the splint could be used with other body tissues and parts that require support by an implantable splint. Therefore, although specific shapes and sizes of the splint are shown and described, the splint could have other shapes and sizes depending upon the particular use of the splint. Further, the splint must be made generally rigid so that the splint retains its relatively straight, flat structure once implanted, thereby providing adequate support to the nasal septum and/or other body tissues.

The invention further relates to a method of supporting a septum by utilizing a pair of dissolvable splints. The splints are made from bioerodable material(s) and are positioned on both sides of the septum to support the septum. The splints are secured to the septum, such as by using a dissolvable suture. The splints and suture thus dissolve over time as the septum heals after surgery thereon, and eventually the splints and suture completely dissolve. Thus, a splint removal procedure is not necessary. The splints have particular use for supporting a nasal septum after a septoplasty procedure, however the dissolvable splints can be used to support other surgically repaired areas of the body as well.

One specific implementation of the invention is illustrated in FIGS. 1–4, with the septal splint being generally referenced by the reference numeral 10. The splint 10 comprises a body having a first side face 12, a second side face 14 and a peripheral edge 16 extending around the body and between the side faces 12, 14. As shown, the splint preferably has an elongated oval shape for use with a nasal septum. The side faces 12, 14 are substantially planar, with the first side face 12 being substantially parallel to the second side face 14.

Figure 2:
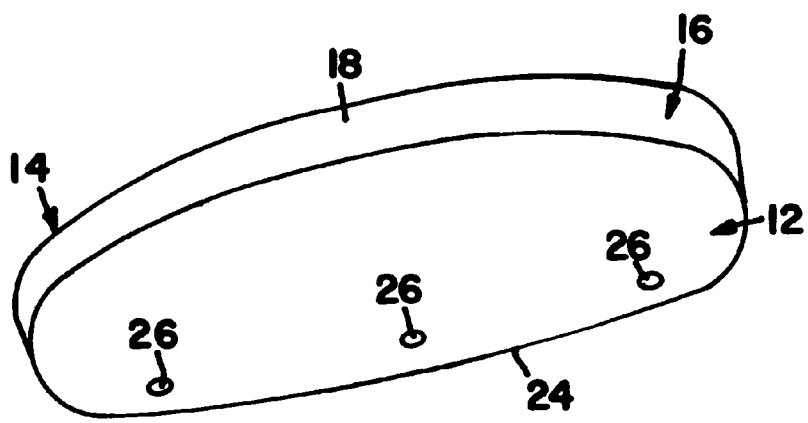
FIG. 2 is a perspective view of the septal splint.

As best seen in FIGS. 1 and 2, the peripheral edge 16 includes a curvilinear section 18 with a first end 20 and a second end 22, and a linear section 24 interconnects and extends between the ends 20, 22, thereby forming the elongated oval shape of the splint 10.

Since the splint 10 provides a support function, it must be made with a sufficient stiffness that will allow the splint 10 to generally maintain its relatively straight, flat overall structure once it is implanted.

Figure 4:
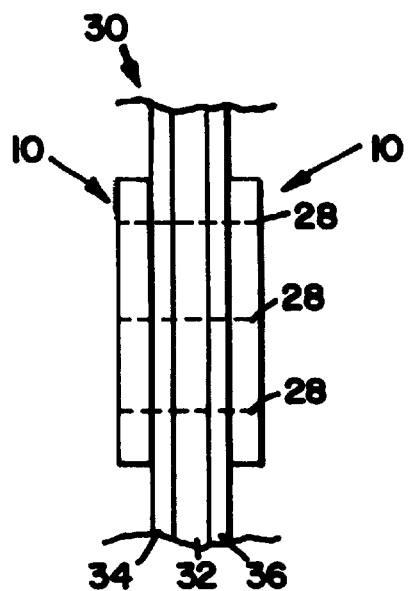
FIG. 4 is a top view of the nasal septum with the septal splints being secured to the septum by dissolvable sutures.

A plurality of holes 26, in this case three holes, are formed through the body and extend from the first side face 12 to the second side face 14. The holes 26 enable passage of a suture 28 through the body for securing the splint 10 to the side of the septum, as shown in FIG. 4. It will be appreciated that a larger or smaller number of holes 26, such as one hole or four holes, may be provided and still be in keeping with the principles of the invention. Furthermore, the body could be formed without any holes, in which case a sharp object, such as a needle, would have to be used to pass the suture 28 through the body.

As described above, the splint 10 is preferably used to support a nasal septum, and therefore the splint 10 is generally sized and shaped for such a use. However, due to differences in anatomy between each patient, the splints will preferably be made in a variety of different shapes and sizes to accommodate each patient. As shown in FIG. 1, the splint 10 has a length l and a height h. It is contemplated that the splint 10 will have three primary sizes, small, medium and large, which should be sufficient to accommodate most patients. The small size splint preferably has a length of about 4.2 cm and a height of about 1.0 cm. The medium size splint preferably has a length of about 4.7 cm and a height of about 1.2 cm. The large size splint preferably has a length of about 5.8 cm and a height of about 2.8 cm. The splint, regardless of its particular size, preferably has a thickness of about 0.25 mm. The surgeon will preferably select the splint size and shape that most closely matches the anatomy of the patient, and the splint is then custom trimmed by the surgeon, using an ordinary operating room scissors or the like, to more closely fit the patient.

In the preferred embodiment of the invention, the splint 10 is made of a material which is bioerodable over a period of time upon exposure to body fluids such as mucus. In one embodiment, the splint 10 might dissolve within four weeks, after which any remaining portions of the splint 10 may be washed away with a saline irrigation.

Preferably, the bioerodable material is collagen, a naturally occurring protein. The collagen is preferably in the form of a gelatin material that is prepared and manufactured in various ways. A splint made from a gelatin collagen material is a generally rigid, slightly malleable device that has some elasticity and memory of structure. These characteristics allow for the splint to be temporarily deformed upon the application of significant force during the positioning of the device. However, in the absence of the force, the splint will return to its original configuration, thus providing a rigid support for the tissue structure to which it is attached.

A preferred gelatin collagen material is called GEL-FILM® which is made by the UpJohn Company of Kalamazoo, Mich. GELFILM® is a material that has been used for many years safely in the middle ear to provide temporary support to structures that have been surgically repaired. GELFILM® is dissolvable over a period of time and its components (collagen, water and nitrogen) are reabsorbed by the body without sequelae. In other forms, the splint 10 is to be made of other forms of collagen and gelatin, not specifically GELFILM®.

The bioerodable material that is used to form the splint 10 can also be impregnated with various material(s). The splint 10 can be impregnated with gluteraldehydes to alter the rate at which the splint 10 dissolves. The splint 10 can also be impregnated with antibiotics which are released as the splint dissolves to assist in the prevention of post-operative infection. The gluteraldehydes and the antibiotics can be used separately, in combination, or not at all, in the splint.

The bioerodable material forming the splint 10 is also preferably dissolvable in certain solvents. Such solvents could be used to irrigate the nasal passages thereby promoting the dissolution of the splint 10. One suitable solvent is saline. If the physician wishes to have the splint dissolve more quickly, saline irrigation can be performed 4–5 times per day. If the splint 10 is to be left in position for the maximum anticipated time period of four weeks, saline irrigation should occur once or twice per day.

Figure 3:
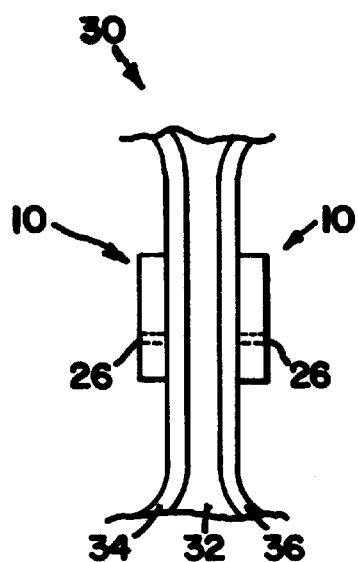
FIG. 3 is a front view of a nasal septum with a pair of the septal splints in accordance with the invention disposed on either side of the septum to provide support for the septum.

The preferred use of the splint 10 will now be described with reference to FIGS. 3 and 4, where a pair of the splints 10 are shown on either side of a nasal septum 30. The septum 30 comprises a central cartilage layer 32, with a layer 34, 36 of mucosa on each side of the cartilage layer 32. The splints 10 are used to support the septum 30 after it has been repaired with a septoplasty procedure. As FIGS. 3–4 show, a splint 10 is positioned on each side of the septum 30 with one side face of each splint abutting the mucosa layers 34, 36. The splints 10 are positioned such that the holes 26 therein are generally aligned with each other. Prior to positioning the splints 10, the splints 10 are trimmed, if necessary, by the surgeon to better fit the patient.

Once the splints are properly positioned, a dissolvable suture(s) 28 is used to secure the splints in place. The suture 28 preferably dissolves over a period of time generally equal to the dissolution time of the splints 10. Like the bioerodable material forming the splints 10, the sutures are preferably dissolvable in solvent such as saline. Such dissolvable sutures are known and need not be further described. If desired, the implanted splints 10 can be impregnated with gluteraldehyde and/or antibiotics.

It will be appreciated that the splint 10 of the invention can be used to support a septum other than a nasal septum, such as the atrial septum and the like, as well as being used to support blood vessel walls, organ walls and other body tissues. In addition, a single splint 10, or more than two splints 10, can be used to support the body tissue, depending upon the particular body tissue.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A septal splint for supporting a nasal septum, comprising:
    a body having first and second side faces and a peripheral edge extending between the first and second side faces, one of said first and second side faces being substantially planar for disposition against the septum, and said body being formed of bioerodable collagen whereby the splint does not have to be surgically removed, wherein the body has first and second side faces and a peripheral edge extending between the first and second side faces, and said peripheral edge includes a curvilinear section with a first end and a second end, and said peripheral edge includes a linear section between the first and second ends, and wherein the body is about 0.25 mm in thickness measured between the first and second side faces.

2. The septal splint according to claim 1, further including at least one hole formed through the body extending from the first side face to the second side face.

3. The septal splint according to claim 2, wherein the body includes a plurality of said holes.

4. The septal splint according to claim 1, wherein both of said first and second side faces are substantially planar, and said first side face is substantially parallel to said second side face.

5. The septal splint according to claim 1, wherein the body is generally rigid.

6. The septal splint according to claim 5, wherein the collagen is in the form of a gelatin material.

7. The septal splint according to claim 1, wherein the body is impregnated with an antibiotic.

8. The septal splint according to claim 1, wherein the body is about 5.8 cm in length and about 2.8 cm in height.

9. The septal splint according to claim 1, wherein the body is about 4.7 cm in length and about 1.2 cm in height.

10. The septal splint according to claim 1, wherein the body is about 4.2 cm in length and about 1.0 cm in height.

11. The septal splint according to claim 1, wherein said body consists essentially of collagen.

12. A method of supporting a nasal septum, comprising:
    providing a pair of septal splints each of which comprises a body having first and second side faces and a peripheral edge extending between the first and second side faces, one of said first and second side faces being substantially planar for disposition against the septum, and each body being formed of bioerodable collagen whereby the splint does not have to be surgically removed, wherein said peripheral edge includes a curvilinear section with a first end and a second end, and said peripheral edge includes a linear section between the first and second ends, and wherein each body is about 0.25 mm in thickness measured between the first and second side faces;
    positioning said septal splints on each side of the nasal septum;
    suturing said septal splints in place with the nasal septum disposed therebetweeen; and
    allowing said septal splints to dissolve over a period of time.

13. The method according to claim 12, wherein suturing comprises suturing said septal splints to the nasal septum using a dissolvable suture.

14. The method according to claim 12, wherein each said septal splint includes a plurality of holes therein, and positioning said septal splints comprises aligning the holes in one of said septal splint with the holes in the other said septal splint.

15. The method according to claim 12, wherein prior to positioning said septal splints, trimming said septal splints to a desired shape.

16. The method according to claim 12, wherein prior to positioning said septal splints, impregnating said septal splints with an antibiotic.

17. The method according to claim 12, further including irrigating said septal splints with a solvent to promote dissolution of said septal splints.

18. The method according to claim 12, wherein providing a pair of septal splints comprises providing septal splints consisting essentially of collagen.

* * * * *